United States Patent
Shimizu et al.

(10) Patent No.: US 7,605,279 B2
(45) Date of Patent: Oct. 20, 2009

(54) PROCESS FOR PRODUCING ALICYCLIC OXETANE COMPOUND

(75) Inventors: Takehiro Shimizu, Fukuoka (JP); Kiyotaka Onishi, Osaka (JP); Hongwen Liu, Fukuoka (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 609 days.

(21) Appl. No.: 10/589,830

(22) PCT Filed: Feb. 15, 2005

(86) PCT No.: PCT/JP2005/002211

§ 371 (c)(1),
(2), (4) Date: Aug. 17, 2006

(87) PCT Pub. No.: WO2005/080364

PCT Pub. Date: Sep. 1, 2005

(65) Prior Publication Data

US 2007/0167637 A1 Jul. 19, 2007

(30) Foreign Application Priority Data

Feb. 23, 2004 (JP) ............................ 2004-046422

(51) Int. Cl.
*C07D 305/06* (2006.01)
(52) U.S. Cl. ..................................... 549/510
(58) Field of Classification Search .................. 549/510
See application file for complete search history.

(56) References Cited

U.S. PATENT DOCUMENTS

2003/0009061 A1 1/2003 Inoue et al.
2003/0231234 A1 12/2003 Ushirogouchi et al.

FOREIGN PATENT DOCUMENTS

| JP | 6-16804 | 1/1994 |
| JP | 6-329569 | 11/1994 |
| JP | 10-204002 | 8/1998 |
| JP | 11-106380 | 4/1999 |
| JP | 11-335314 | 12/1999 |
| JP | 2000-302774 | 10/2000 |
| JP | 2001-31664 | 2/2001 |
| JP | 2001-31665 | 2/2001 |
| JP | 2002-80581 | 3/2002 |
| JP | 2002-322268 | 11/2002 |
| JP | 2004-2668 | 1/2004 |
| JP | 2004-233635 | 8/2004 |

*Primary Examiner*—Bernard Dentz
(74) *Attorney, Agent, or Firm*—Edwards Angell Palmer & Dodge LLP

(57) ABSTRACT

Provided is a production process by which a novel alicyclic oxetane compound which has an oxetane ring, has excellent light transmission in the near ultraviolet region, and is useful as a cationically polymerizable monomer can be easily obtained. The production process which is for obtaining an alicyclic oxetane compound includes subjecting an aromatic oxetane compound to nuclear hydrogenation in high-pressure hydrogen in the presence of a hydrogenation catalyst. For example, when 4,4'-bis[(3-ethyloxetan-3-yl)methoxymethyl]biphenyl is used as the aromatic oxetane compound, 4,4'-bis[(3-ethyloxetan-3-yl)methoxymethyl]bicyclohexyl is obtained as the alicyclic oxetane compound.

4 Claims, No Drawings

PROCESS FOR PRODUCING ALICYCLIC OXETANE COMPOUND

TECHNICAL FIELD

The present invention relates to a process for producing an alicyclic compound having at least two oxetane rings (hereinafter referred to as the "alicyclic oxetane compound").

BACKGROUND ART

Examples of a prior document related to the present invention include the following documents.

Patent Document 1: DE 1021858 A
Patent Document 2: U.S. Pat. No. 5,750,590
Patent Document 3: JP-A-11-106380
Patent Document 4: EP 1,069,120 A
Patent Document 5: JP-A-2002-80581
Patent Document 6: JP-A-2000-302774
Patent Document 7: JP-A-2003-55359
Non Patent Document 1: H. Sasaki and J. V. Crivello, J. Macromol. Sci., Part A-Pure Appl. Chem. (Marcel Dekker, Inc.), 1992, A29(10), P. 915-930
Non Patent Document 2: J. V. Crivello and H. Sasaki, J. Macromol. Sci., Part A-Pure Appl. Chem. (Marcel Dekker, Inc.), 1993, A30(2&3), P. 189-206

A compound having an oxetane ring (hereinafter referred to as the "oxetane compound") is a compound that has been attracting attention in recent years because it functions as a monomer which can be subjected to photoinitiating cationic polymerization or which can be cured. In particular, a polyfunctional oxetane compound having two or more oxetane rings in one molecule is known to show high reactivity (see, for example, DE 1021858 A).

DE 1021858 A describes, as an example of a polyfunctional oxetane compound that has been conventionally reported, an aromatic compound having two or more oxetane rings (hereinafter referred to as the "aromatic oxetane compound") and represented by a general formula (7):

[Chem 1]

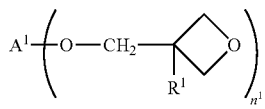

(7)

where $A^1$ represents an aromatic residue which is divalent or more, $R^1$'s each represent a hydrogen atom or an organic residue, and $n^1$ represents an integer larger than 1.

In addition, various polyfunctional aliphatic and aromatic oxetane compounds have been disclosed in, for example, J. Macromol. Sci., Part A-Pure Appl. Chem. 1992, A29 (10), P. 915-930 and J. Macromol. Sci., Part A-Pure Appl. Chem. 1993, A30 (2 & 3), P. 189-206, U.S. Pat. No. 5,750,590, JP-A-11-106380, EP 1,069,120 A, and JP-A-2002-80581.

In addition, JP-A-2000-302774 discloses alicyclic oxetane compounds serving as a 1,4-cyclohexanedimethanol derivative and a 4,8-bis(hydroxymethyl)tricyclo[5,2,1,0$^{2,6}$]decane derivative, and a process for producing each of them. However, the production process has a problem in that a production step is so complicated that a production cost is high because the process involves: converting 3-alkyl-3-hydroxymethyloxetane into a sulfonate once; reacting the resultant sulfonate and a diol with each other in the presence of a base; and isolating the resultant through vacuum distillation.

Furthermore, JP-A-2003-55359 discloses a process for producing a bis(hydroxymethyl)tricyclo[5,2,1,0$^{2,6}$]decane derivative having an oxetane ring. However, the production process, which involves reacting 3-alkyl-3-chloromethyloxetane and a bis(hydroxymethyl)alicyclic compound with each other in the presence of an alkali, is not sufficiently satisfactory because the yield of a target product is low owing to a low reaction rate and a side reaction.

DISCLOSURE OF THE INVENTION

Problems to be Solved by the Invention

An object of the present invention is to provide a process by which an alicyclic oxetane compound which: has excellent light transmission in the near ultraviolet region; and is useful as a novel cationically polymerizable monomer which provides a cured product excellent in heat resistance, toughness, and adhesiveness and showing small shrinkage on curing and which brings together high reactivity and appropriate fluidity at normal temperature can be advantageously produced. Another object of the present invention is to provide a process for producing an alicyclic oxetane compound that can be synthesized from an easily available raw material.

MEANS FOR SOLVING THE PROBLEMS

That is, the present invention relates to a process for producing an alicyclic oxetane compound represented by the following general formula (2), the process being characterized by including subjecting a divalent to tetravalent structural unit having an aromatic ring and an aromatic ring of an aromatic oxetane compound having at least two oxetane rings, and represented by the following general formula (1) to nuclear hydrogenation:

[Chem 2]

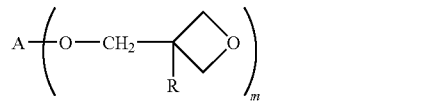

(1)

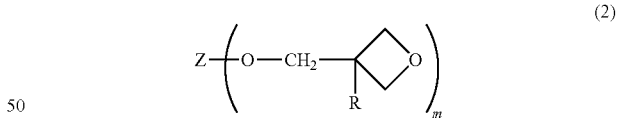

(2)

in the general formulae (1) and (2), m represents an integer of 2 to 4, R's each represent an alkyl group having 1 to 6 carbon atoms, A represents a divalent to tetravalent aromatic residue represented by any one of the following general formulae (3) to (5), and Z represents an alicyclic residue produced by hydrogenation of the aromatic residue represented by A:

[Chem 3]

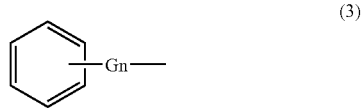

(3)

-continued

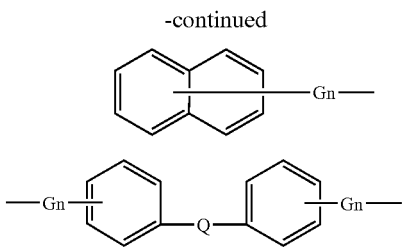

(4)

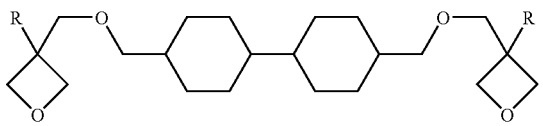

(5)

in the general formulae (3), (4), and (5), G's each represent a single bond, a methylene group, an ethylene group, or an ethylidene group, Q represents a single bond, an oxygen atom, a methylene group, an ethylene group, an ethylidene group, or an isopropylidene group, n represents a number of G's by which an aromatic ring is substituted and independently represents an integer of 2 to 4, and a total of n's in the general formula (5) represents an integer of 2 to 4.

At this point, as the alicyclic oxetane compound represented by the general formula (2), an oxetane compound represented by the following general formula (6) is preferably exemplified:

[Chem 4]

(6)

where R's each represent an alkyl group having 1 to 6 carbon atoms.

Further, the present invention relates to a process for producing the alicyclic oxetane compound in which the nuclear hydrogenation is performed in a presence of a catalyst containing at least one kind of a metal selected from the group consisting of Ni, Co, Ru, Rh, Pd, Os, Ir, and Pt and in a presence of a hydrogen gas having a pressure of 1 MPa (gauge pressure) in the range of 50 to 250° C.

Hereinafter, the present invention will be described in detail.

A starting material to be used in the production process of the present invention is an aromatic oxetane compound represented by the general formula (1). A compound obtained by the production process of the present invention is an alicyclic oxetane compound represented by the general formula (2).

In the general formulae (1) and (2), common symbols represent the same, m represents an integer of 2 to 4, and R's each represent an alkyl group having 1 to 6 carbon atoms. Preferably, m represents 2, and R's each represent a methyl group or an ethyl group in terms of relatively easy availability of a raw material. In the general formula (1), A represents a divalent to tetravalent aromatic residue represented by any one of the general formulae (3) to (5). In the general formula (2), Z represents an alicyclic residue produced from A mentioned above.

In the general formulae (3) to (5), G's each represent a single bond, a methylene group, an ethylene group, or an ethylidene group, and Q represents a single bond, an oxygen atom, a methylene group, an ethylene group, an ethylidene group, or an isopropylidene group. An aromatic ring is substituted by n. G's, and n's (when two n's are present in a formula, the total of n's) each independently represent an integer of 2 to 4. When the total of n's represents an integer of 2 to 4 in the general formula (5), one n may represent 0 or 1. n in each of the general formulae (3) and (4), and the total of n's in the general formula (5) each correspond to m in each of the genera formulae (1) and (2). It should be noted that when an aromatic ring is substituted by n G's, n G's may be identical to or different from each other.

In the general formulae (3) to (5), G's each preferably represent a single bond or a methylene group, and Q preferably represents a single bond, an oxygen atom, a methylene group, or an isopropylidene group, or more preferably represents a single bond.

In an alicyclic oxetane compound obtained by the production process of the present invention, an aromatic residue represented by any one of the general formulae (3), (4), and (5) is subjected to nuclear hydrogenation to become an aliphatic residue. The aliphatic residue may be completely subjected to nuclear hydrogenation, or only part of the residue may be subjected to nuclear hydrogenation; provided that preferably 50% or more, more preferably 90% or more, or still more preferably 99% or more of the residue is subjected to nuclear hydrogenation. In addition, an alicyclic oxetane compound obtained by subjecting an aromatic residue represented by one of the general formulae (4) and (5) to nuclear hydrogenation is a novel compound as well.

Next, examples of the alicyclic oxetane compound obtained by the production process of the present invention and represented by the general formula (2) will be shown. Alicyclic oxetane compounds in each of which Z in the general formula (2) is represented by any one of the following general formulae (11) to (14) are preferably exemplified.

[Chem 5]

(11)

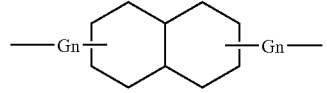

(12)

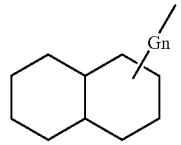

(13)

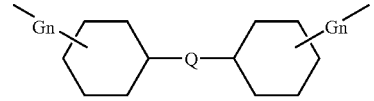

(14)

In the general formulae (11) to (14), n's (when two n's are present in a formula, the total of n's) each represent an integer of 2 to 4. One n in each of the general formulae (12) and (14) may represent 0 or 1. In addition, G's and Q each have the same meaning as that described in each of the general formulae (3), (4), and (5).

A preferable alicyclic oxetane compound is an alicyclic oxetane compound represented by the general formula (6). Formulae (15) to (19) and Table 1 show other preferable alicyclic oxetane compounds. In Table 1, R means any one of R's in the general formula (2), and G means any one of G's in the formulae (15) to (19). It should be noted that the formulae (15) to (17) each correspond to an example in which n or the total of n's in each of the general formulae (11) to (13) represents 2 while the formulae (18) and (19) each correspond to an example in which, in the general formula (14), n's each represent 1 and Q represents a single bond or a methylene group.

In Table 1, Compounds Nos. 1 to 6 show examples of a compound of the formula (15), Compounds Nos. 7 to 10 show examples of a compound of the formula (17), Compounds Nos. 11 to 18 show examples of a compound of the formula (16), Compounds Nos. 19 and 20 show examples of a compound of the formula (18), and Compounds Nos. 20 and 21 show examples of a compound of the formula (19).

TABLE 1

(Structural formulae (15)–(19) shown)

| Compound No. | R | G | Substitution position of G | formula |
|---|---|---|---|---|
| 1 | Me | single bond | 1,4 | 15 |
| 2 | Et | single bond | 1,4 | 15 |
| 3 | Me | single bond | 1,3 | 15 |
| 4 | Et | single bond | 1,3 | 15 |
| 5 | Me | $CH_2$ | 1,3 | 15 |
| 6 | Et | $CH_2$ | 1,3 | 15 |
| 7 | Me | single bond | 1,4 | 17 |
| 8 | Et | single bond | 1,4 | 17 |
| 9 | Me | $CH_2$ | 1,4 | 17 |
| 10 | Et | $CH_2$ | 1,4 | 17 |
| 11 | Me | single bond | 1,5 | 16 |
| 12 | Et | single bond | 1,5 | 16 |
| 13 | Me | $CH_2$ | 1,5 | 16 |
| 14 | Et | $CH_2$ | 1,5 | 16 |
| 15 | Me | single bond | 2,6 | 16 |
| 16 | Et | single bond | 2,6 | 16 |
| 17 | Me | $CH_2$ | 2,6 | 16 |
| 18 | Et | $CH_2$ | 2,6 | 16 |
| 19 | Me | single bond | 4,4' | 18 |
| 20 | Et | single bond | 4,4' | 18 |
| 21 | Me | $CH_2$ | 4,4' | 19 |
| 22 | Et | $CH_2$ | 4,4' | 19 |

The production process of the present invention is a process for producing an alicyclic oxetane compound involving subjecting an aromatic oxetane compound to nuclear hydrogenation. Any known method can be adopted for nuclear hydrogenation; provided that a method involving performing hydrogenation with a hydrogen gas in the presence of a catalyst is advantageous. The catalyst to be used in the hydrogenation reaction, which is not particularly limited as long as it has hydrogenation activity for an aromatic ring, desirably contains at least one kind of a metal selected from the group consisting of Ni, Co, Ru, Rh, Pd, Os, Ir, and Pt. Each of those metals may be in a metal state, or may be turned into a compound such as an oxide on condition that each of them has hydrogenation activity.

The above catalyst may be used after a carrier has been caused to carry the catalyst. Examples of the carrier include: crystalline or non-crystalline metal oxides or composite oxides such as silica, alumina, silica-alumina, titania, zirconia, various zeolites, and diatomaceous earth; carbonaceous substances such as activated carbon, graphite, and carbon black; and a mixture of two or more kinds of them. Of those, silica, alumina, or a carbonaceous substance is preferable. The shape of a carried catalyst is not particularly limited, and a carried catalyst of an arbitrary shape such as a powdery shape, a pellet-like shape, or a fibrous shape can be used.

Although the above hydrogenation reaction proceeds even in the absence of a solvent, a solvent may be used in the reaction. The solvent is not particularly limited as long as it does not inhibit the hydrogenation reaction. From the viewpoint of the solubility of each of a raw material and a reaction product, any one of: alcohol-based solvents such as 2-propanol and cyclohexanol; ether-based solvents such as tetrahydrofuran (THF) and dioxosilane; ester-based solvents such as ethyl acetate and butyl acetate; and glycol ether-based solvents such as ethylene glycol monobutyl ether, propylene glycol monomethyl ether, and propylene glycol monomethyl ether acetate is preferably used.

The hydrogenation reaction is performed in the reaction temperature range of 50 to 250° C. Although a reaction (hydrogen absorption) velocity increases with increasing temperature, the ratio of a side reaction such as decomposition tends to increase with increasing temperature. Accordingly, the reaction temperature is in the range of preferably 80 to 200° C., or particularly preferably 100 to 160° C. The hydrogenation reaction is performed at a reaction pressure of 1 MPa (gauge pressure) or more, and there is no particular upper limit for the reaction pressure. From the viewpoints of, for example, a device cost and safety, a pressure of 20 MPa (gauge pressure) or less, or preferably 10 MPa (gauge pressure) or less is recommended. A reaction time desirably ends on the completion of the absorption of a hydrogen gas except for the case where partial nuclear hydrogenation is an object. The reaction time is ordinarily in the range of 1 to 20 hr.

After the completion of the hydrogenation reaction, the catalyst and the solvent are separated, and the remainder is purified by means of, for example, distillation or recrystallization as required, whereby a target alicyclic oxetane compound is obtained.

BEST MODE FOR CARRYING OUT THE INVENTION

Hereinafter, the present invention will be specifically described by way of examples. However, the scope of the present invention is not limited to these examples. It should be noted that the term "purity" in the following description refers to a value for an area percentage provided by gas chromatography analysis unless otherwise stated. In addition, the term "pressure" refers to a gauge pressure.

EXAMPLE 1

40 g of 4,4'-bis[(3-ethyloxetan-3-yl)methoxymethyl]biphenyl (obtained by subjecting ETERNACOLL OXBP manufactured by UBE INDUSTRIES, LTD.; purity 94.6%) to a pretreatment for removing a reaction inhibiting substance), 60 g of ethyl acetate as a solvent, and 0.2 g of a 5% Ru-carbon carried catalyst (manufactured by N.E. CHEMCAT CORPORATION, powder) were loaded into an electromagnetic stirring type autoclave having an internal volume of 200 ml, and the autoclave was hermetically sealed. After that, the inside of the autoclave was replaced with a nitrogen gas three times and with a hydrogen gas three times, and then the pressure in the autoclave was increased to 6 MPa with the hydrogen gas. A temperature was increased while stirring was performed. A hydrogenation reaction was performed while an inner temperature of 140° C. and an inner pressure of 6 MPa were kept. The stirring was stopped 1 hour after no hydrogen absorption had been observed. The time elapsed between the initiation of the temperature increase and the stopping of the reaction was about 6 hours. After having been cooled, the reaction liquid was extracted and analyzed by means of gas chromatography. As a result, the resultant compound had a purity of 87.3%, the percentage consisting of 45.8% of a trans-trans isomer, 35.1% of a trans-cis isomer, and 6.4% of a cis-cis isomer. After the catalyst had been filtered out, the solvent and a decomposition by-product were distilled off under reduced pressure and heating, whereby a colorless, transparent, viscous liquid having a purity of 94.7% was obtained. The viscous liquid had a viscosity (25° C.) of 1.4 Pa·s. The results of various instrumental analyses are shown below.

FD-MS: 422 (molecular weight). $^1$H-NMR (CDCl$_3$ solvent, TMS standard (0 ppm)): δ (ppm); 0.88 (t, J=7.4 Hz, 6H, CH$_3$—CH$_2$), 1.3 to 1.9 (m, 20H, CH$_2$& CH (cyclohexane ring)), 1.74 (q, J=7.6 Hz, 4H, CH$_3$—CH$_2$), 3.23 to 3.38 (d (4 kinds), J=6.3 to 7.1 Hz, 4H, cyclohexyl-CH$_2$—O), 3.50 & 3.52 (s & s, 4H, O—CH$_2$—C), 4.38(d, J=5.9 Hz, 4H, O—CH$_2$—C (oxetane ring)), 4.45 & 4.46 (d & d, J=5.9 & 5.6 Hz, 4H, O—CH$_2$—C (oxetane ring)).

$^{13}$C-NMR (CDCl$_3$ solvent, solvent standard (77 ppm): δ (ppm); 8.2 (CH$_3$—CH$_2$), 25.7-26.2 (CH$_2$(cyclohexane ring)), 26.4 & 26.8 (CH$_3$—CH$_2$), (CH$_2$(cyclohexane ring)), 29.5 to 30.2 (CH$_2$(cyclohexane ring)), 34.6 to 41.6 (CH(cyclohexane ring)), 43.5 (C), 73.6 (O—CH$_2$—C(oxetane ring), 74.3 & 74.6 (cyclohexyl-CH$_2$—O), 78.6 (O—CH$_2$—C(oxetane ring).

FT-IR (castfilm method): 829, 981 cm$^{-1}$ (cyclic ether), 1110 cm$^{-1}$ (chain ether).

The above analyses identified the resultant compound as 4,4'-bis[(3-ethyloxetan-3-yl)methoxymethyl]bicyclohexyl corresponding to the case where R's in the general formula (6) each represented an ethyl group.

EXAMPLE 2

A reaction was performed in the same manner as in Example 1 except that a 5% Ru-alumina carried catalyst (manufactured by N.E. CHEMCAT CORPORATION; powder) was used. The time elapsed between the initiation of the temperature increase and the stopping of the reaction was about 6 hours. The reaction liquid was analyzed by means of gas chromatography. As a result, the resultant compound had a purity of 88.1%, the percentage consisting of 44.6% of a trans-trans isomer, 36.5% of a trans-cis isomer, and 7.0% of a cis-cis isomer.

EXAMPLE 3

12.8 g (0.11 mol) of 3-ethyl-3-hydroxymethyloxetane having a purity of 98.5%, 4.5 g (0.11 mol) of an NaOH powder having a purity of 97%, and 25 ml of toluene were loaded into a 300-ml three-necked round bottom flask equipped with a temperature gauge, a condenser, a stirring device, and a dropping funnel, and the whole was stirred at 90° C. for 30 minutes under heating. A solution prepared by dissolving 11.5 g (0.05 mol) of a bis(chloromethyl)naphthalene mixture composed of 45.5% of 1,4-bis(chloromethyl)naphthalene and 53.4% of 1,5-bis(chloromethyl)naphthalene into 175 ml of toluene was dropped from the dropping funnel to the resultant over 30 minutes. Furthermore, a reaction was continued at 90° C. for 10 hours. After the completion of the reaction, the temperature of the reaction mixture was cooled to room temperature, and the precipitate was filtered out. The filtrate and a washed liquid obtained by washing the precipitate with 20 ml of toluene twice were gathered, and the whole was washed with 100 ml of water three times. The oil phase of the resultant was separated, and the remainder was added with sodium sulfate to be dried. After that, toluene was distilled off under reduced pressure, whereby 15.3 g of a pale yellow crystal were obtained. The analysis of the crystal by means of gas chromatography confirmed that: the resultant compound had a purity as a bisoxetane compound of 86.2%; and the yield of the compound was 68.6%. 10.0 g of the crystal were dissolved into 10.0 g of toluene under heating, and the temperature of the solution was cooled to room temperature. Then, purification was performed through recrystallization. After having been filtered out, the crystal was dried under reduced pressure, whereby 2.3 g of a pale yellow crystal were obtained. The crystal had a purity as a bisoxetane compound of 95.6% (1,4-isomer:1,5-isomer=28:72).

A hydrogenation reaction was performed in the same manner as in Example 2 except that: 2.0 g of bis[(3-ethyloxetan-3-yl)methoxymethyl]naphthalene (mixture of a 1,4-isomer and a 1,5-isomer) thus obtained and 48 g of ethyl acetate as a solvent were used; and an inner pressure was changed to 10 MPa. The time elapsed between the initiation of the temperature increase and the stopping of the reaction was about 12 hours. The analysis of the reaction liquid by means of gas chromatography confirmed that the purity of bis[(3-ethyloxetan-3-yl)methoxymethyl]decahydronaphthalene (isomer mixture) was 75.5%.

INDUSTRIAL APPLICABILITY

According to the production process of the present invention, an alicyclic oxetane compound can be easily obtained in high yield. In addition, the alicyclic oxetane compound obtained by the production process of the present invention is characterized in that it brings together high reactivity and appropriate fluidity at normal temperature. In addition, the compound has excellent light transmission particularly in the near ultraviolet region because the compound is substantially free of a color radical such as an aromatic ring. At the same time, the compound is useful as a novel cationically polymerizable monomer which provides a cured product excellent in heat resistance because the compound has an alicyclic structure in its main chain. Furthermore, the cured product is characterized in that: it is excellent in toughness, adhesiveness, and the like; and it shows small shrinkage on curing. Because of those reasons, the alicyclic oxetane compound obtained by the production process of the present invention is useful as a coating material, an adhesive material, an electronic material, a dental material, and the like.

The invention claimed is:

1. A process for producing an alicyclic oxetane compound represented by the following general formula (2), which comprising subjecting an aromatic ring of an aromatic oxetane compound having at least two oxetane rings and represented by the following general formula (1) to nuclear hydrogenation:

[Chem 1]

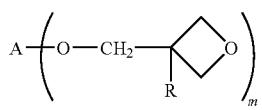

(1)

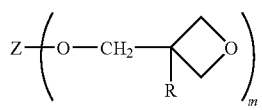

(2)

in the general formulae (1) and (2), m represents an integer of 2 to 4, R represents an alkyl group having 1 to 6 carbon atoms, A represents a divalent to tetravalent aromatic residue represented by any one of the following general formulae (4) to (5), and Z represents an alicyclic residue produced by hydrogenation of the aromatic residue represented by A:

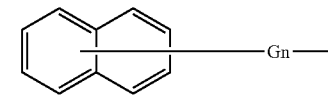

(4)

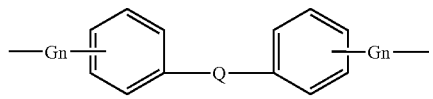

(5)

in the general formulae (4), and (5), G represents single bond, methylene group, ethylene group, or ethylidene group, Q represents single bond, oxygen atom, methylene group, ethylene group, ethylidene group, or isopropylidene group, n represents a number of G by which an aromatic ring is substituted and represents an integer of 2 to 4 in each of the general formulae (4), and a total of n in the general formula (5) represents an integer of 2 to 4.

2. A process for producing an oxetane compound according to claim 1, wherein the alicyclic oxetane compound represented by the general formula (2) comprises an oxetane compound represented by the following general formula (6):

(6)

[Chem 3]

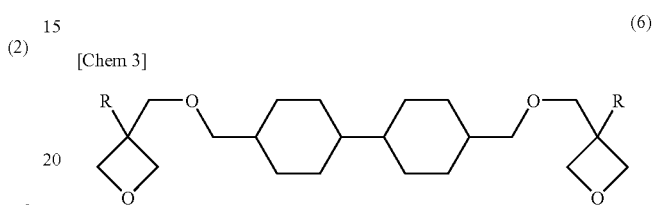

where R represents an alkyl group having 1 to 6 carbon atoms.

3. A process for producing an oxetane compound according to claim 1, wherein the nuclear hydrogenation is performed in a presence of a catalyst containing at least one kind of a metal selected from the group consisting of Ni, Go, Ru, Rh, Pd, Os, Ir, and Pt and in a presence of a hydrogen gas having a pressure of 1 MPa (gauge pressure) or more at 50 to 250° C.

4. A process for producing an oxetane compound according to claim 2, wherein the nuclear hydrogenation is performed in a presence of a catalyst containing at least one kind of a metal selected from the group consisting of Ni, Go, Ru, Rh, Pd, Os, Ir, and Pt and in a presence of a hydrogen gas having a pressure of 1 MPa (gauge pressure) or more at 50 to 250° C.

\* \* \* \* \*